(12) United States Patent
Coffinardi et al.

(10) Patent No.: US 12,290,112 B2
(45) Date of Patent: *May 6, 2025

(54) SOCK WITH FUNCTIONAL BIOMECHANICAL, CIRCULATORY AND NEUROLOGICAL EFFICACY

(71) Applicant: Coffinardi & Delpanno Industrie Srl, Brescia (IT)

(72) Inventors: Marco Coffinardi, Brescia (IT); Alessandro Coffinardi, Brescia (IT); Piero Delpanno, Brescia (IT); Mauro Testa, Brescia (IT)

( * ) Notice: Subject to any disclaimer, the term of this patent is extended or adjusted under 35 U.S.C. 154(b) by 91 days.

This patent is subject to a terminal disclaimer.

(21) Appl. No.: 17/997,690

(22) PCT Filed: May 11, 2021

(86) PCT No.: PCT/IB2021/054014
§ 371 (c)(1),
(2) Date: Nov. 1, 2022

(87) PCT Pub. No.: WO2021/229440
PCT Pub. Date: Nov. 18, 2021

(65) Prior Publication Data
US 2023/0165316 A1    Jun. 1, 2023

(30) Foreign Application Priority Data
May 13, 2020   (IT) .................. 102020000010843

(51) Int. Cl.
*A41B 11/00*           (2006.01)
(52) U.S. Cl.
CPC .......... *A41B 11/008* (2013.01); *A41B 11/003* (2013.01); *A41B 2500/10* (2013.01)

(58) Field of Classification Search
CPC ... A41B 11/008; A41B 11/007; A41B 11/003; A61F 13/08; D04B 1/26
See application file for complete search history.

(56) References Cited

U.S. PATENT DOCUMENTS 4,397,161 A * 8/1983 Chesebro, Jr. ......... A41B 11/00
66/178 A
5,263,923 A * 11/1993 Fujimoto ......... A41D 19/01582
602/62

(Continued)

FOREIGN PATENT DOCUMENTS

| EP | 3575463 | 12/2019 |
|---|---|---|
| JP | 2007175465 | 7/2007 |
| WO | 2013003434 | 1/2013 |

*Primary Examiner* — Jillian K Pierorazio
(74) *Attorney, Agent, or Firm* — Themis Law

(57) ABSTRACT

A sock or similar garment includes a foot part and a leg part, the foot part being designed to overlap the foot of a user and the leg part being designed to overlap at least part of the leg up to below the knee. Optionally, the foot part is closed by a toe part. The sock has, in one or more areas of its surface extension, one or more structural modification elements of at least one layer of the knitting that forms the wall of the stock. Those modification elements may be applied with different techniques, for example, printed with silk-screen, or incorporated or intertwined into or on the structure of the sock's mesh, and are configured to enhance the functionality of the leg and foot according to biomechanical, circulatory and neurological aspects, harmonizing those effects with each other, obtaining therapeutic efficacy and providing prevention and performance enhancement.

12 Claims, 8 Drawing Sheets

(56) References Cited

U.S. PATENT DOCUMENTS

| | | | | |
|---|---|---|---|---|
| 5,412,957 A * | 5/1995 | Bradberry | A61F 13/08 | 66/178 A |
| 5,640,714 A * | 6/1997 | Tanaka | A41B 11/00 | 2/22 |
| 5,708,985 A * | 1/1998 | Ogden | D04B 1/04 | 66/178 R |
| 5,898,948 A * | 5/1999 | Kelly | A41B 11/00 | 2/239 |
| 7,748,240 B1 * | 7/2010 | Cherneski | A41B 11/008 | 66/185 |
| 8,973,411 B2 * | 3/2015 | Gaither | A61F 13/08 | 2/241 |
| 10,724,157 B2 * | 7/2020 | Zorn | D02G 3/32 | |
| 10,799,414 B1 * | 10/2020 | Higgins | A61H 1/00 | |
| 2005/0144703 A1 * | 7/2005 | Hilbert | A41B 11/008 | 2/239 |
| 2009/0276939 A1 * | 11/2009 | Sho | D04B 1/26 | 66/178 A |
| 2011/0015668 A1 * | 1/2011 | Cros | D04B 1/265 | 606/201 |
| 2011/0061149 A1 * | 3/2011 | Polacco | A43B 13/223 | 2/241 |
| 2011/0302699 A1 * | 12/2011 | Kaneda | D04B 1/26 | 2/239 |
| 2011/0314591 A1 * | 12/2011 | Mitsuno | D04B 1/265 | 2/239 |
| 2012/0058316 A1 * | 3/2012 | Cherneski | A41B 11/008 | 427/288 |
| 2013/0131572 A1 * | 5/2013 | Cros | A61F 13/00987 | 602/75 |
| 2014/0053610 A1 * | 2/2014 | Fukui | D04B 1/102 | 66/178 A |
| 2014/0331387 A1 * | 11/2014 | Hennings | A41B 11/003 | 2/239 |
| 2015/0119781 A1 * | 4/2015 | Ponce | A61H 1/0237 | 602/28 |
| 2015/0173428 A1 * | 6/2015 | Langer | A41D 31/18 | 2/242 |
| 2016/0166419 A1 * | 6/2016 | Jones | A43B 7/1445 | 602/66 |
| 2017/0311650 A1 * | 11/2017 | Hupperets | A41B 11/00 | |
| 2017/0354543 A1 * | 12/2017 | Mazourik | A61H 1/008 | |
| 2018/0021199 A1 * | 1/2018 | Halbrecht | A61F 5/0127 | 601/27 |
| 2018/0051401 A1 * | 2/2018 | Giorgini | A41B 11/02 | |
| 2018/0317565 A1 * | 11/2018 | Mccuaig | A41B 11/007 | |
| 2018/0325196 A1 * | 11/2018 | Miller | D06M 23/16 | |
| 2018/0353345 A1 * | 12/2018 | Sasaki | D04B 1/22 | |
| 2018/0368484 A1 * | 12/2018 | Baravarian | A41B 11/02 | |
| 2019/0029331 A1 * | 1/2019 | Field | A41B 11/003 | |
| 2019/0082746 A1 * | 3/2019 | Storelli | A41B 11/008 | |
| 2019/0153639 A1 * | 5/2019 | Nishigaki | A41B 11/003 | |
| 2019/0239572 A1 * | 8/2019 | Abbey | A41B 11/007 | |
| 2019/0289956 A1 * | 9/2019 | Eugene | A43B 7/1475 | |
| 2020/0100927 A1 * | 4/2020 | Eugene | A61F 5/019 | |
| 2020/0214365 A1 * | 7/2020 | Varsik | A41B 11/008 | |
| 2020/0221791 A1 * | 7/2020 | Gazit | A41B 11/008 | |
| 2020/0345086 A1 * | 11/2020 | Langer | A41D 13/0015 | |
| 2020/0347530 A1 * | 11/2020 | Tannebaum | D04B 1/04 | |
| 2021/0071329 A1 * | 3/2021 | Cummings | D04B 21/16 | |
| 2022/0047005 A1 * | 2/2022 | Arciuolo | A41B 11/003 | |
| 2022/0125128 A1 * | 4/2022 | Blecha | D06M 23/04 | |
| 2022/0125646 A1 * | 4/2022 | Hsiao | A41B 11/003 | |
| 2022/0167687 A1 * | 6/2022 | Gazit | A41B 11/02 | |

* cited by examiner

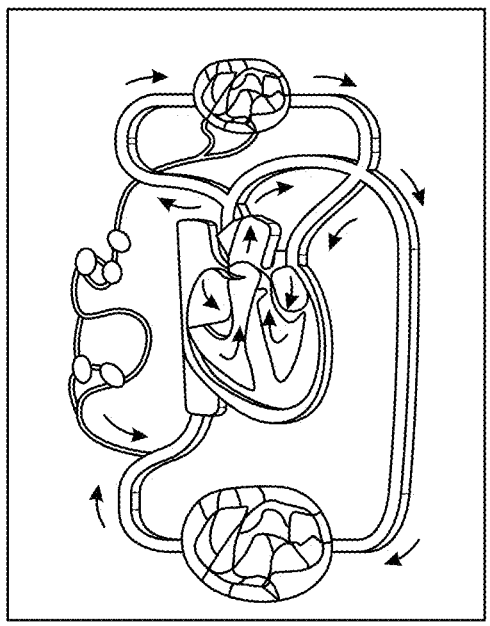
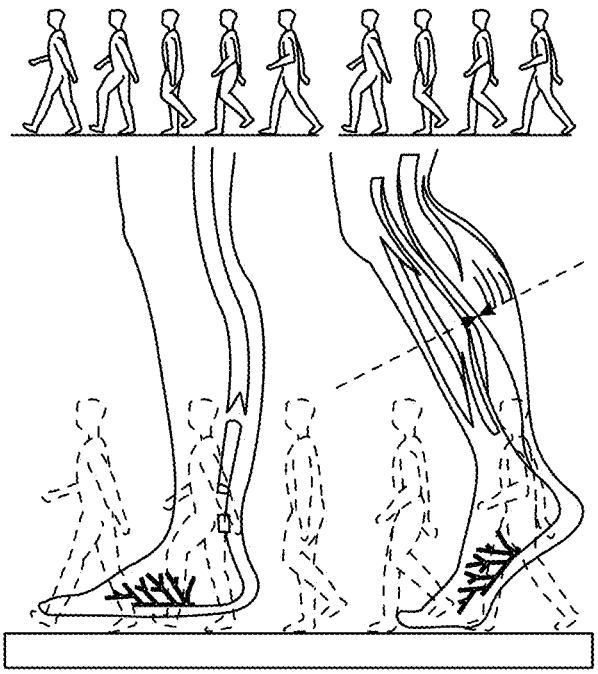
FIG. 1.1                    FIG. 1.2
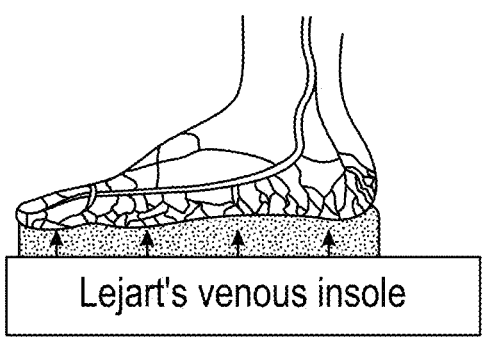
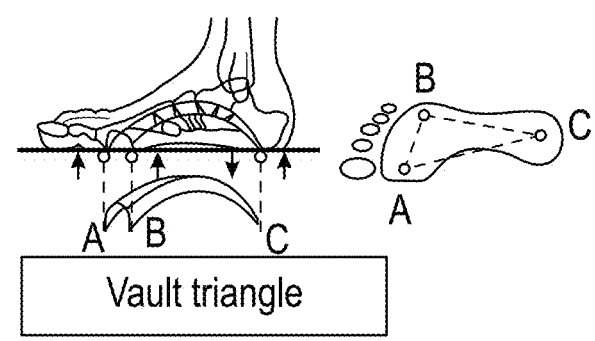
FIG. 1.3                    FIG. 1.4

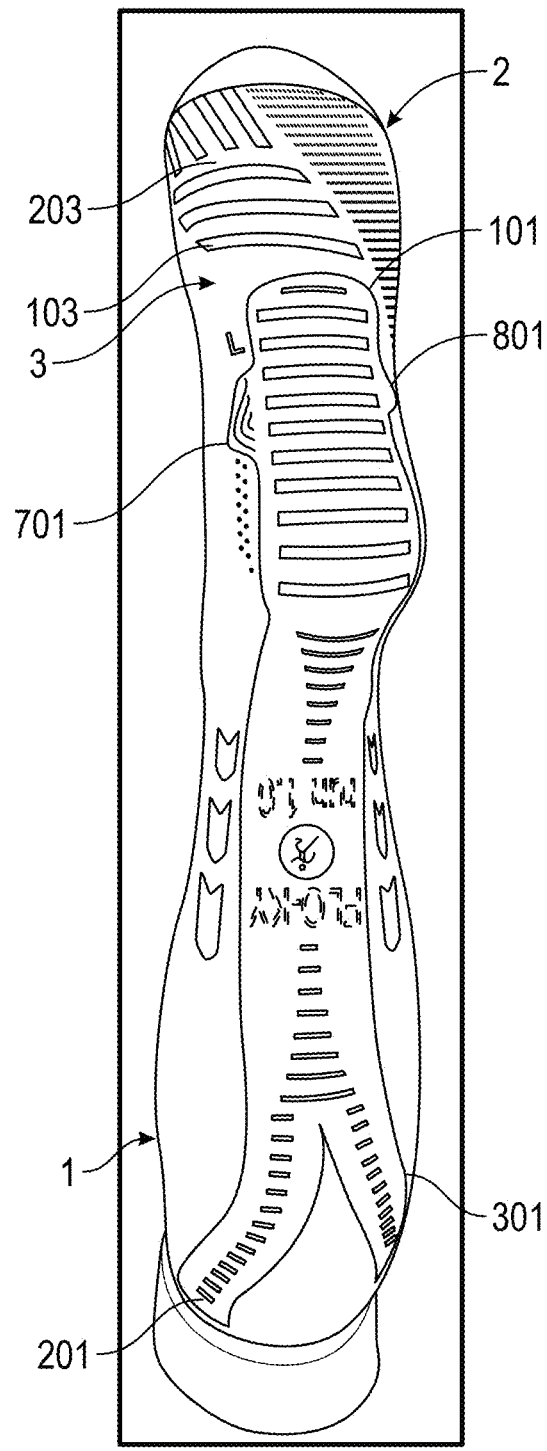
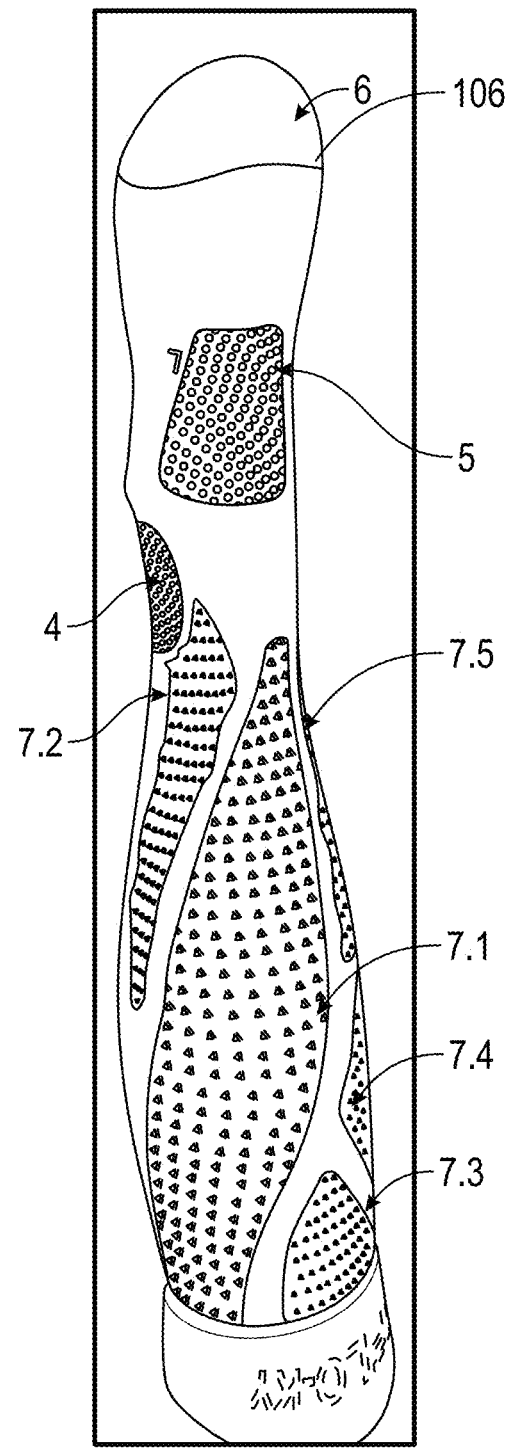
FIG. 4                    FIG. 5

SOCK WITH FUNCTIONAL BIOMECHANICAL, CIRCULATORY AND NEUROLOGICAL EFFICACY

FIELD OF THE INVENTION

The invention refers to a sock or similar garment, comprising
a part of foot and a part of leg,
the foot part being designed to overlap the foot of a user and the leg part being designed to overlap at least one part or the whole part of the leg up to below the knee;
optionally the foot part being closed by a toe part,
said sock presenting in one or more areas of the extension of its surface one or more elements of structural modification of at least one layer of the knitted fabric which forms the wall of said sock, which elements are applied and/or incorporated and/or intertwined and/or incorporated in or are in the structure of said fabric.

BACKGROUND OF THE INVENTION

Socks of this type are known in the state of the art. The Japanese document JP2007/175465 describes, for example, a sock with a so-called "taping" effect, that is a sock on which at least a strip or an island of material in the form of a layer or film is applied, having a predetermined shape, a predetermined extension, a predetermined position with respect to the anatomy of the foot and of the leg when the sock is worn and predetermined characteristics of elastic deformability, both in relation to extension in one or more directions, and in relation to flexion or bending.

The taping technique involves the application in the form of tapes or islands of tape-like material. This type of tape is known as kinesiotape. Most commonly, kinesiotape consists of tightly woven cotton and nylon fibers. Said tape is applied to the skin in defined points according to the desired physiotherapeutic action by means of glues, for example acrylic glue, resistant to water so that adhesion to the body is guaranteed even in the case of vigorous movements, sweat and total immersion in water and without irritating the skin.

In the state of the art it is known to provide a sock with one or more compression zones of corresponding zones of the leg and/or of the foot. Document US2017/0354543 describes a garment, and in particular a sock that has one or more zones distributed over its extension aimed at compressing the corresponding leg and/or foot zone. In this exemplary embodiment, the compression zones are formed by islands or bands of material which are superimposed and/or woven and/or incorporated into the knit that forms the sock and which has a different hardness and/or deformability and/or extensibility with respect to the fabric of the sock.

In the state of the art it is also known to provide a sock which comprises coupled, woven, braided and/or incorporated anti-slip material, in particular provided on the outer face of the sock material and intended to increase the friction between the sock and the shoe. Such a sock is known from US2005/0144703.

EP3575463 describes a sock comprising a wall made of compressive knitted fabric and which carries on the internal face in contact with the foot or the leg a padding made in such a way that in the worn condition of the sock said padding is arranged between the two heads of the gastrocnemius muscle.

The padding also extends to the part of the foot in correspondence of which foot it assumes a shoe-like conformation that substantially covers the whole foot, that is the sole of the foot, the area of the toes both below and above and laterally and part of a lower lateral band of the foot, without generating areas with different biomechanical functionality for the different areas of the foot.

US2018368484 discloses a sock having one or more support elements for providing structural support to one or more regions of the wearer's foot. A support element is able to overlap the entire arch of the foot, without interruption from the heel area to the area of the roots of the phalanges and said element extends even partially continuously around the external or internal side of the foot up to reach the median area of the instep. Typically, said support element has an elasticity coefficient lower than an elasticity coefficient of the other areas of the sock. This support element of the plantar arch area is not able to provide differentiated support actions between the various areas of the foot, generating dynamic relationships between them that correspond to the dynamics of the musculoskeletal and vascular structure of the foot, but the support element is identical in mechanical characteristics for the entire extension that covers different anatomical areas of the foot, exerting the same mechanical effect for each of them.

WO2013003434 discloses a foot cover comprising a three-dimensional portion printed on a fabric material and formed from an elastomeric material. Said cover has a shoe shape and covers the entire foot both for the upper and for the lower part, said cover is printed without interruption for 360° around the foot. The printed portion also preferably includes openings or perforations within the area of the printed portion for breathability. The sole part of said cover has grip or anti-slip elements distributed according to a predetermined pattern on it.

In all these solutions known to the state of the art, the shape, the dimensions and the mechanical characteristics of the material that forms the support zones, the compression zones and the anti-slip zones as well as the arrangements and distributions of these zones along the extension of the sock are not achieved in a way that is harmonized with the biomechanics of the leg and of the foot, but each of these areas performs a specific function without the same being accorded to the function of the other areas in order to satisfy the biodynamic needs of the leg and of the foot.

Biomechanics is the science that studies human movement and the mechanisms to optimize it, making it not only more pleasant but healthy and free from risk of injury.

The venous return and the general well-being of the body that originates from the function of the foot is primary interest for the biomechanical, the lymphatic return is closely linked to the venous return, this is the body's "scavenger", that is the system that eliminates waste due to our metabolism or those produced by physical exercise as waste or oxidation elements. So, the recovery after a workout or a competition is part of the foot function but it is also correct to say that health starts from the foot and its function.

The most abused area of the body is certainly that of the lower limbs and in particular our feet, of which we only remember when they are painful. In reality, the foot is much more than a simple anatomical structure that allows locomotion.

In fact, despite appearances, the foot is not limited only to supporting the body weight in an upright position. Its vascularization and relative innervation allow it to play an important physiological role, while its osteo-articular structure allows it to adapt to any situation of static or dynamic equilibrium. It can therefore be considered a real body that actively participates in its functions.

The venous plantar plays an indispensable role in the venous system of the lower limbs. The blood pumped by the heart towards the distal extremities of the body must subsequently rise despite many obstacles: the distance, which cancels the initial pressure effect at the heart level and the gravity which tends to favor stagnation in the vessels farthest from the heart. The venous return is instead favored by the upright position which causes the contraction of the lower limbs, favoring a real massage of the veins (FIG. 1.2). During the march is added the compression of the plantar veins that empty with each step. As evidence of this, the color of the skin becomes white under the support areas of the foot. There is a whole system of communication between the plantar veins and the dorsal veins, which facilitates the venous return from the deep network (FIGS. 1.1 to 1.4).

However, since the lower limbs do not benefit from the direct thrust of a pulsating pump like the heart, the venous return is mainly achieved thanks to 2 structures:

Lejars venous insole (FIG. 1.3): the dynamic contraction of this structure favors the action of muscle pump and therefore the return of blood to the upper districts. However, it is a "bed" of very small capillaries that contains a small amount of blood, this is placed in the meso foot.

The triangle of the Vault (FIG. 1.4): an architectural structure, located in the deepest part of the foot, which contains the most important deep veins: the internal and external plantar veins. The squeezing of these veins, at each significant step and movement, represents the true peripheral heart and the most important vascular function of the foot, the triangle is the area of the medial foot and the support of the first and fifth toes.

The blood returns to the heart by pressure gradient, that is, from where there is more pressure to where there is less. Standing we have a pressure in the Lejars venous insole of 35 mm of Hg versus 0 mm of Hg of the heart.

Venous return is the retrograde flow that brings blood back to the heart. In resting conditions, the venous return must be equal to the cardiac output, because the cardiovascular system is essentially a closed circuit. Otherwise, the blood would accumulate either in the systemic circulation or in the pulmonary circulation; Although cardiac output and venous return are interdependent, each of them can be adjusted independently. The circulatory system (FIG. 1.1) is in fact made up of two circulations (pulmonary and systemic) placed in series between the right ventricle (VD) and the left ventricle (VS). The equilibrium is achieved, in large part, by Frank Starling's law. In hemodynamics, the venous return to the heart from the venous vascular bed, located in the midfoot is determined by a pressure gradient (venous pressure right atrial pressure) and by venous resistance: in fact, a decrease in the right atrial pressure or venous resistance will lead to an increased venous return, except when changes are determined by posture. It could equally well be said that venous return is determined by mean aortic pressure and mean right atrial pressure, divided by systemic vascular resistance. To clarify the somewhat confused picture of the terms used to define venous return, some physiologists correlate it to the more measurable influences of cardiac output, such as pressure and end-diastolic volume which are in turn influenced by the volume status, by the venous capacity, ventricular compliance and venodilating therapies.

As it appears from the above, the solutions currently present in the state of the art do not fully satisfy the biomechanical needs of the foot and leg as each of these are oriented towards the support of only one of the biomechanical functions described above.

SUMMARY OF THE INVENTION

The invention aims to produce a garment and in particular a sock, which, thanks to relatively simple and easily implemented measures, provides an improved support of all the biomechanical functions linked to the foot and the leg, allowing, on the one hand, to avoid the negative effects due to an incorrect or intense solicitation of the foot and leg both from the musculoskeletal point of view and from the circulatory and neurological point of view and on the other hand, to operate in support of all the functions of the foot and of the leg particularly related to proprioception, to the optimization of the stresses on muscles and tendons and to circulatory and neurological functions and therefore transforming physical activity into a mechanism that generates a beneficial healing activity.

The invention solves the above problem with a garment, particularly a sock comprising:
  a part of foot and a part of leg,
  the part of the foot being intended to overlap a user's foot and the part of the leg being designed to overlap at least a part or the whole part of the leg up to below the knee.
  optionally the foot part being closed by a toe part,
  said sock presenting in one or more areas of the extension of its surface one or more elements of structural modification of at least one layer of the knitted fabric which forms the wall of said sock, which elements are applied and/or incorporated and/or intertwined and/or incorporated in or in the structure of said fabric.

According to a first aspect of the invention, the elements of modification of the structure of the sock consist of an element of thickening of the wall of the sock which extends for substantially the entire plantar vault of the foot or substantially along the entire Lejars venous insole and/or substantially along the entire triangle of the vault of the foot.

According to one embodiment, the said thickening extends, optionally without interruption, up to the insertion area of the Achilles tendon.

Still according to a further embodiment, the said element extends over the part of the quarter which has a length such as to also overlap the calf area, possibly extending up to below the knee, optionally without interruption, the extension of the said element extending up to the calf area.

In one embodiment, the said extension of the element in correspondence with the calf area is divided into two branches that diverge each other towards the corresponding lateral area of the leg.

In a non-limiting embodiment, the two extension branches of said element after the bifurcation extend respectively upwards and in such a way as to follow the conformation of the calf muscles, i.e. in particular so that a branch of the bifurcation is in correspondence of the medial twin muscle and the other branch at the level of the lateral twin muscle.

In a variant embodiment, the leg is of the type corresponding to that of the so-called "American stocking", in which the leg ends in the initial lower area of the calf, that is the root of the Achilles tendon and does not extend so as to cover the calf itself, in this case, the said thickening element extends along the said quarter for substantially the entire length of the same, or up to the root of the Achilles tendon.

An embodiment provides that said thickening element is constituted by a continuous band or strip of material having a predetermined width and a predetermined thickness, and which band of material preferably extends seamlessly from the front end of the foot vault, that is the extremity towards the metatarsals, up to the opposite extremity and in particular to the extremities of the two branches of the bifurcation when said thickening element extends up to and along the calf area.

In the aforesaid case, therefore, the said thickening element extends substantially along the entire arch of the foot, around the heel and beyond in correspondence with the area of insertion of the Achilles tendon and possibly beyond up to the calf area and as indicated in one previous embodiments also along the calf itself.

According to an embodiment, the said thickening element is made substantially as described in the previous document PCT/IB2019/060212.

In this case, the thickening element according to the present invention is formed by a band or a strip of material associated with the knitted wall of the sock in the area intended to overlap the anatomical areas previously described, i.e. the arch of the foot, or the Lejars venous insole and/or triangle of the vault, the area of insertion of the Achilles tendon and possibly the calf, the material of which band has a lower extensibility than the extensibility of the remaining wall of the stocking.

According to a still further feature, said band or strip is made of plastic material, preferably silicone and especially silicone with memory or other elastically flexible and/or deformable materials preferably provided with shape memory. Other possible materials are made of polyurethane, PVC, or a fabric.

Advantageously, said band or strip of material is applied to the outside of the knitted fabric that forms the wall of the sock.

Still according to one feature, the overall width of the band or strip is between 1 cm and 8 cm, more preferably between 2 cm and 6 cm to ensure correct support and sustain for the ankle joints and its soft tissues.

Preferably, each support strip has a thickness of at least 50 μm to ensure optimal support, without being too rigid at the same time.

As will appear in greater detail in the following description, the knitted fabric wall of the stocking can be made of an elasticized fabric and/or being made by knitting processes to obtain a compression effect, preferably of graduated compression. Furthermore, in some embodiments, the fabric can have different types of weaves that modify its thickness and/or stiffness, in particular with reference to its extensibility and shape memory, or to the elastic return force in the condition not subjected to tension of extension.

According to yet another feature, in order to obtain a transpiring effect, the thickening element, or the band or strip of material, can have a perforated or micro-perforated structure that allows proper transpiration. These holes or micro-holes can be provided in the material of the band or strip that forms the thickening element and possibly also in the fabric wall of the sock.

According to still a further embodiment, the stocking is of the tubular type and therefore a pre-formed area of the stocking corresponding to the heel is missing.

According to a further embodiment, the aforementioned thickening element, or the band or strip that constitutes it, can be provided with at least one lateral extension towards the inner side of the foot and in correspondence with the plantar arch area. An executive variant provides that this lateral extension is provided in the median area of the longitudinal extension of the plantar arch.

This extension may have a different or identical thickness to that of the remaining part of the thickening element and/or can also optionally be made of an identical or different material.

In a further embodiment which can be provided in combination with one or more of the previous embodiments and variants, the said thickening element is provided with at least one lateral extension towards the external side of the foot.

An variant embodiment provides that said extension is provided to coincide substantially with the root of the fifth metatarsal and/or in a substantially opposite position and possibly substantially aligned along a lateral-lateral axis of the foot.

Thanks to the above features, the sock according to the present invention allows to maximize the localized compression on the Lejars venous insole and on the triangle of the vault, improving the effect on circulation.

Thanks to its mechanical characteristics, the thickening element also confers an effect similar to that of the so-called "taping" or "elastic therapeutic tape" otherwise also known as Kinesiotape. (see https://en.wikipedia.org/wiki/Elastic_therapeutic_tape; https://it.wikipedia.org/wiki/Taping).

In particular, the taping effect gives protection to the plantar aponeurosis and stimulates it upwards, increasing the squeezing effect of the vault itself.

When the aforementioned extension is provided on the internal side of the foot, further support of the plantar arch is generated, while when the aforementioned internal extension of the foot is provided, a support effect is generated on the root of the V metatarsus.

The thickening element at the insertion area of the Achilles tendon has the advantageous function of minimizing the vibrations due to the contact of the foot with the ground.

According to a further aspect of the present invention, in combination with one or more of the preceding embodiments, the part of fabric which forms the wall of the sock in the area of the sole of the foot is associated with further elements for modifying the structure of said wall which are distributed according to a predetermined design and which have differentiated effects between them in order to reproduce and therefore support the propeller movement of the foot during running and walking.

According to a first embodiment, an element of thickening of the wall of the stocking corresponding and coincident with the area of the 5th metatarsal is applied to the sock.

In a variant embodiment, this thickening element is made similarly to the thickening elements previously described and coinciding with the Lejars venous insole and the further anatomical districts.

According to a further embodiment, the thickening element further presents high friction to increase the grip of the said area of the foot with the shoe.

In combination with this embodiment and the corresponding variants, in the area of the first metatarsal and possibly also of the corresponding phalanges, anti-slip zones or of augmented grip between the sock and the shoe are provided between the terminal end of the thickening element coinciding with the plantar arch and the said phalanges.

Said zones consist of material with a high friction coefficient such as for example rubber, silicone or similar plastic materials in correspondence with which zones the said material is applied to the layer of fabric which forms the wall of the sock.

According to an embodiment, the said areas are made with a design such as to favor an anti-slip or greater grip action between the sock and the shoe which are such as to favor the helical movement of the foot during the running or walking, in combination with the effect of thickening the area of the 5th metatarsal thanks to the thickening element coinciding with it.

The preferred design for this effect foresees a first zone coinciding with the foot end which has a band or strip oriented transversely to the longitudinal extension of the phalanx, a following intermediate zone which extends substantially in the connection zone of the phalanges with the first metatarsal and which has one or preferably more strips or bands oriented in a direction substantially parallel to the longitudinal extension of the phalanges and a terminal zone flanked at the end of the thickening element coinciding with the foot vault which is constituted by one or preferably two or more strips or bands of non-slip material oriented transversely to the longitudinal extension of the phalanges.

According to an embodiment, the said strips or bands of anti-slip material oriented transversely to the longitudinal extension of the phalanges and provided alongside the end of the thickening element coinciding with the foot vault extend from the internal lateral limit of the foot towards a median zone of the same and terminate with their ends coinciding along an ideal line oriented obliquely with respect to the longitudinal extension of the foot, so that the strip closest to the thickening element coinciding with the foot vault ends substantially flush with the edge of the said thickening strip facing the external side of the foot, while the furthest one ends substantially in a central area of the width of the foot, or in correspondence with the second and/or third metatarsal.

With reference to a still further feature, the intermediate zone between that provided with the bands or strips of anti-slip material and the end of the thickening element in the plantar arch area and the thickening zone in correspondence with the 5th metatarsal can possibly be equipped with a distribution of disks of non-slip material distributed according to a rectangular distribution grid.

According to a further characteristic, the sock is further provided with further anti-slip or increased friction zones (with respect to the friction coefficient of the sock fabric) which are associated with further parts of the foot and/or leg.

According to one embodiment, the sock has non-slip zones, i.e. provided with elements with a higher friction coefficient than the material of the fabric that forms the sock, alternatively or in combination, in the areas of the sock coinciding with the outside of the ankle and/or with the dorsal part of the foot coinciding with the tongue of the shoe.

According to an embodiment, the said strips or bands or said points of non-slip material, or with a coefficient of friction greater than that of the material of the sock fabric, are made by applying, for example by printing, for example by silk-screen printing of the said material on the sock fabric.

The type of material can be identical from area to area or can vary from area to area of application of said anti-slip material, as well as the thickness of the material applied to the fabric of the sock.

According to yet another embodiment which can be provided in any combination or sub-combination with one or more of the previous embodiments and/or the previous variants, the fabric forming the sock can have a different structure in different areas of the same which areas are associated with predetermined anatomical areas of the leg or of the foot. This structure can be obtained by modifying the type of weaving of the knitted fabric in the corresponding zone so as to obtain a zone of greater thickness and/or of greater mechanical resistance to traction and therefore a greater elastic force of return in the condition not subjected to traction. According to a particular embodiment, the said areas of greater thickness and/or mechanical resistance and/or elastic coefficient are provided to coincide with the areas of the tibial and/or peronal musculature.

A specific embodiment provides that said areas have a spindle-shaped position and shape that corresponds to that of a muscle bundle or a group of muscle bundles of the tibial and/or peronal area.

Thanks to the aforementioned features according to the different variants that can be provided alternately or in any combination between them, the sock according to the present invention harmonizes in a precise way the different conditions for optimizing the biomechanical functions of the foot and leg, especially for those who want to practice sports both at an amateur and professional level. In fact, the aforementioned features favor physical exercise itself, preserving the structures of the body as much as possible.

The sock according to the present invention produces multiple benefits during use in the performance of physical exercise:

Improved localized compression on the Lejars venous insole resulting in:
1) better muscle oxygenation and faster recovery;
2) less muscle fatigue and pain typical of efforts;
3) increase in muscle power;
4) better resistance;
5) reduction of the risk of injury to the muscle fibers;

Non-slip function:
1) less slipping of the foot in the shoe;
2) increase of proprioception with the road surface;
3) lower risk of retorts;
4) greater awareness of stability;
5) better thrust in running and walking;

"Taping" and shimming function:
1) increased squeezing also in the calf area and greater muscle oxygenation;
2) decrease in vibrations with consequent lower possibility of inflammation of the Achilles tendon;
3) decrease in calf fatigue;
4) less chance of falling of the 5th metatarsal, and improvement of posture during running;
5) protection from vibrations due to contact with the ground and therefore protection against microtraumas;
6) increase of the binding on the back of the shoe and therefore increase of the stability during running;
7) unloading of the Achilles tendon with reduction of effort during running
8) thicknesses of the thickening and anti-slip areas distributed on the sole of the foot and such as to reproduce the propeller effect of the foot thus favoring the movement of the foot during running and thus creating an aid in motion and therefore an improvement in performance Applications of the thickening elements and/or the anti-slip material by silk-screen printing on the external side of the knitted fabric of the sock:
1) thanks to external applications, no thread or layer of material extends inside the sock and therefore the possibility of blistering is reduced;
2) thanks to external applications, a lighter sock is generated with consequent less sweating of the foot, consequently decreasing the possibility of skin maceration effects;
3) the provision of non-slip silk-screened areas on the back and near the ankle optimizes the grip with the shoe, preventing the sock from rolling and the consequent loss of improving functions.

According to another feature that can be provided in combination with any of the previous embodiments, any of the currently known artisanal and/or industrial manufacturing techniques can be used to manufacture the garment described above.

One embodiment provides for the manufacture by means of a circular knitting or hosiery machine, which comprises a cylinder which can be selectively activated in rotation to perform a series of total or partial rotations with continuous or reciprocating motion.

In this case, the sock is made by constructing a substantially tubular body having a first end and a second end and comprising a leg portion, a foot portion and an optional toe portion.

The various thickening elements and the areas of non-slip material are applied as described above and associating at least one strip, a band or points of material to an area of the external surface of the tubular body by molding and/or gluing, application, hot application, screen printing.

According to a variant embodiment, the sock can be constructed entirely with continuous motion, except for the construction of a possible portion of the tip, which can be constructed with alternating motion. Therefore, the sock is constructed in a continuous motion also at the level of the portion to be worn on the heel, unlike the normal construction of a sock or the like, for which the construction of the heel is provided to take place in alternating motion.

Alternatively, and advantageously, the sock can be constructed with any method and with the aid of any device that allows to obtain a substantially tubular body, in which the tubular body.

In an alternative embodiment, the sock can also be made starting from a piece of fabric, comprising, or to which is associated, at least a strip, a band or an area of thickening and/or anti-slip material and which piece is sewn so as to define a substantially tubular garment.

In one embodiment, the use of a so-called GREEN fabric is envisaged, that is to protect the environment, for example a fabric obtained from the recycling of bottles.

When seams are provided, such as for example in the closing area of the toe part, these are in the form of external seams and in particular reinforcing for a better durability of the product and above all to avoid the creation of blisters on the toes.

Still according to a further embodiment which can be provided in any combination with one or more of the preceding characteristics, the fabric of the sock can be constituted by a light fabric with side openings to improve sweat escape.

BRIEF DESCRIPTION OF THE DRAWINGS

The invention will become clearer from the following description of a non-limiting executive example illustrated in the attached figures, in which:

FIGS. 1.1 to 1.4 show the human circulatory system and the effects on circulation of squeezing the veins in the calf area, the Lejars venous insole and the vault triangle.

FIG. 4 and FIG. 5 show a left sock according to FIGS. 2 and 3 in worn condition and respectively a view on the rear side and one on the front side.

DETAILED DESCRIPTION OF EMBODIMENTS OF THE INVENTION

Figure 2:
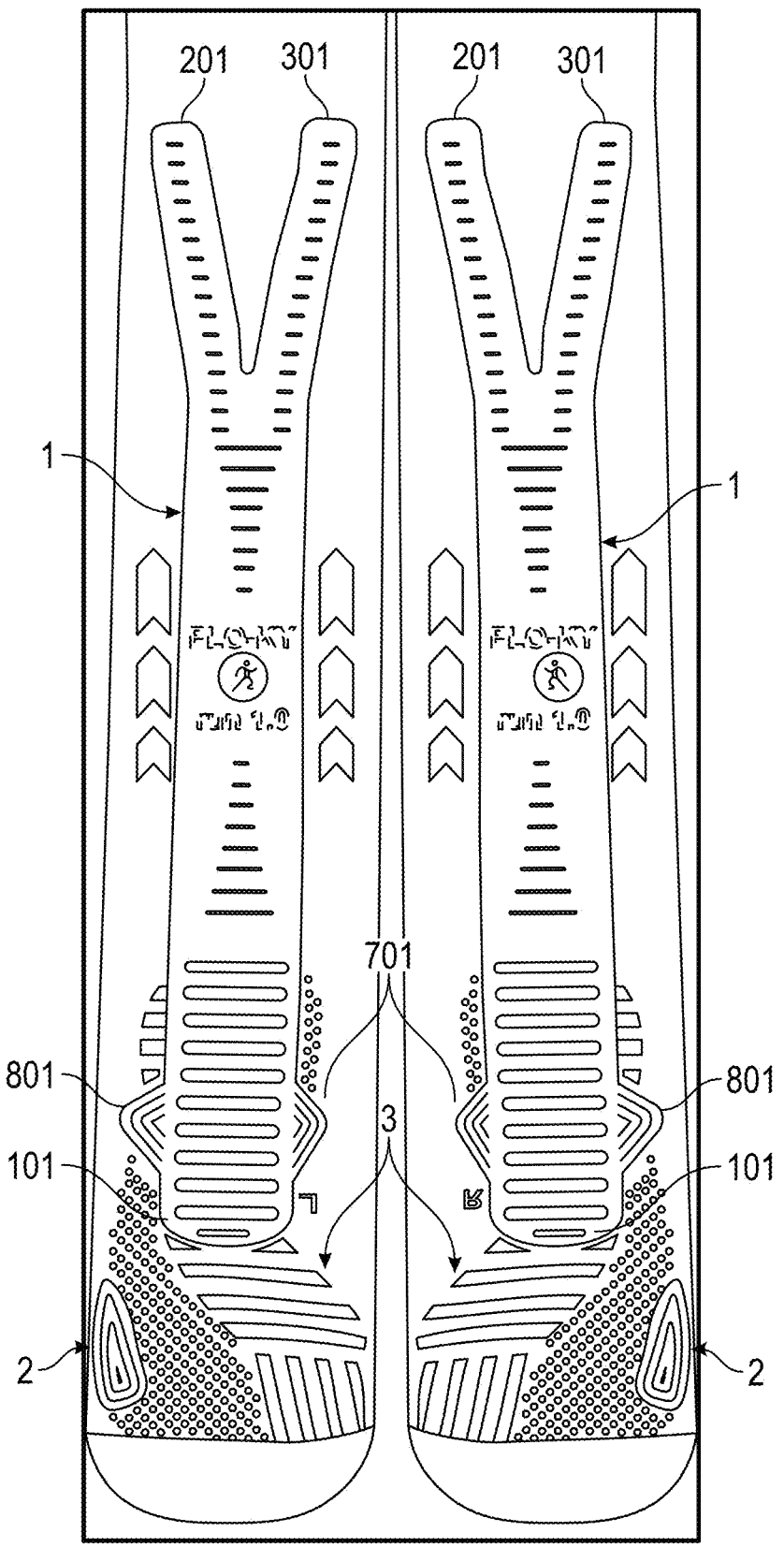
FIG. 2 shows a right and left pair of socks according to the present invention in an unworn condition and with a view on the rear side of the sock.
Figure 3:
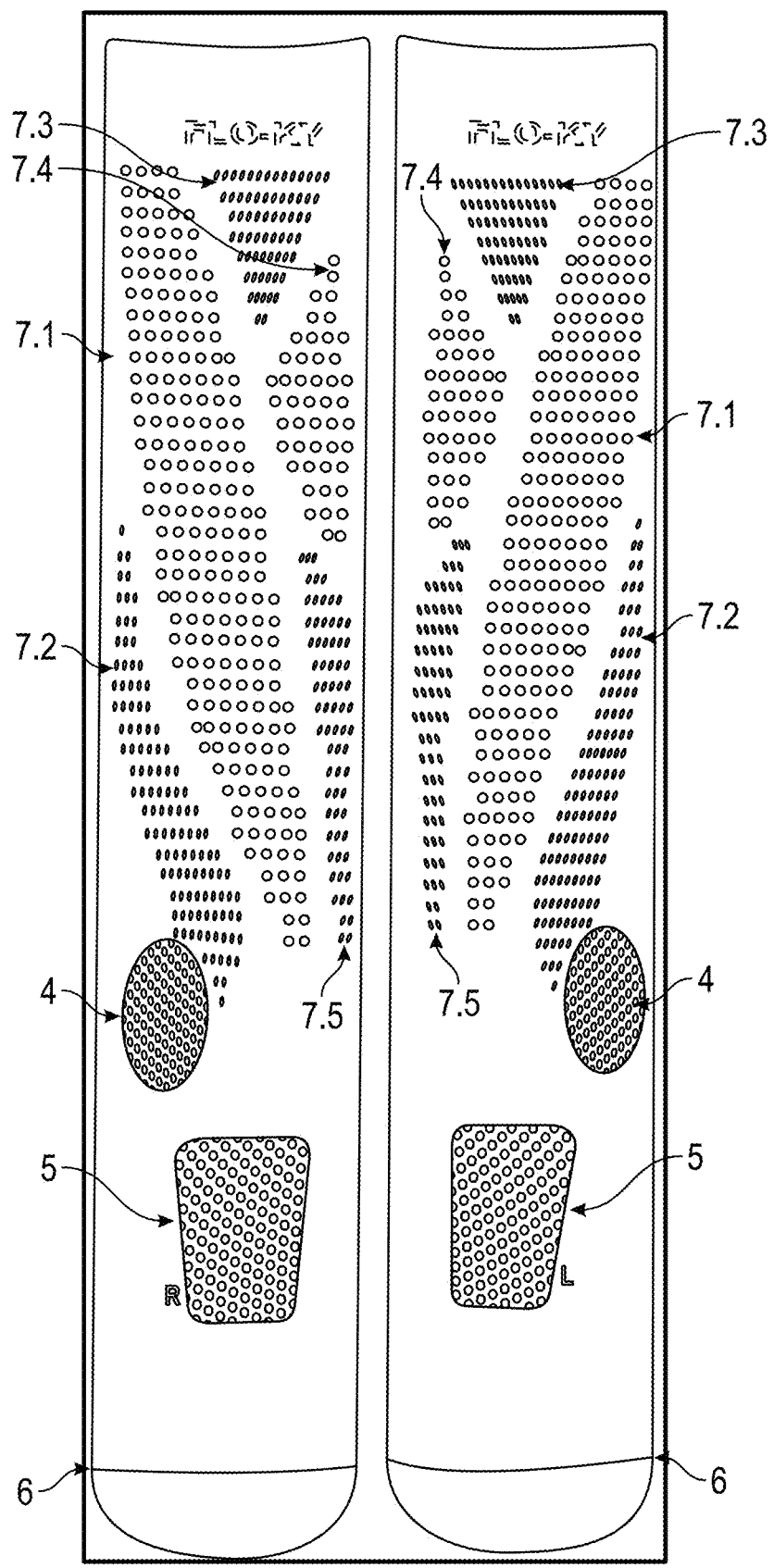
FIG. 3 shows a front side view of the socks of the pair of socks of FIG. 2.
Figure 6:
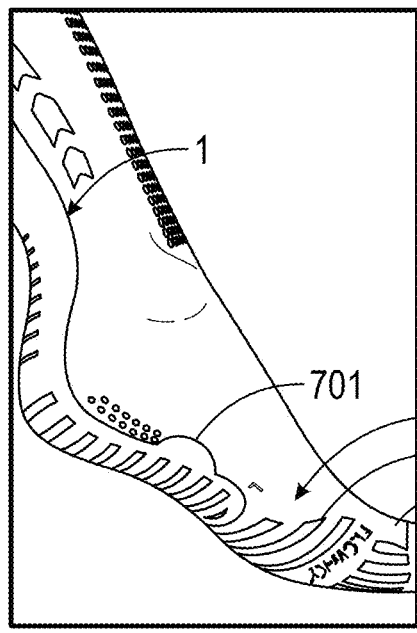
FIGS. 6 to 9 show various details of the foot area of the sock according to the previous figures, in worn condition.
Figure 7:
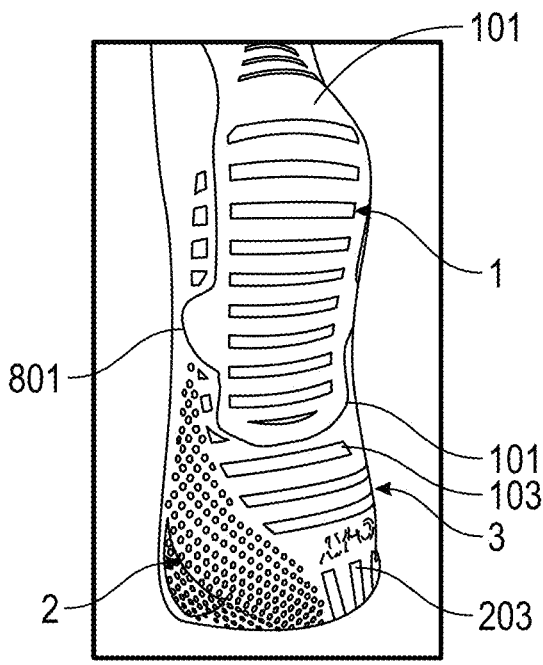
Figure 8:
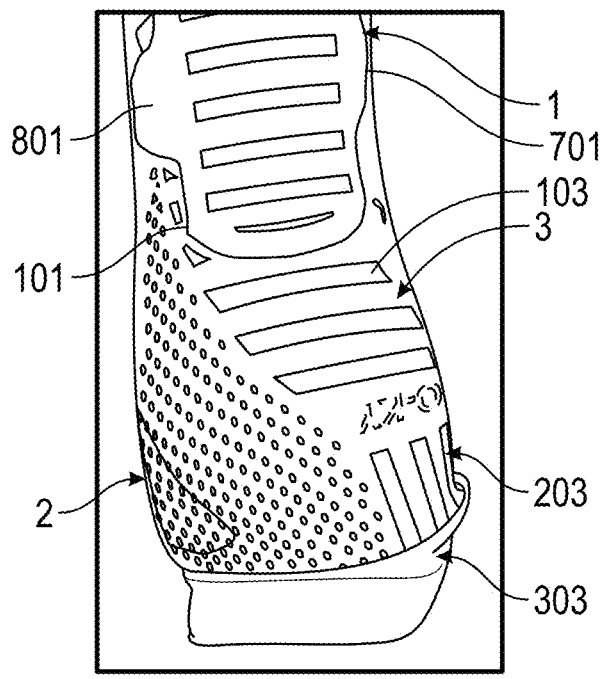
Figure 9:
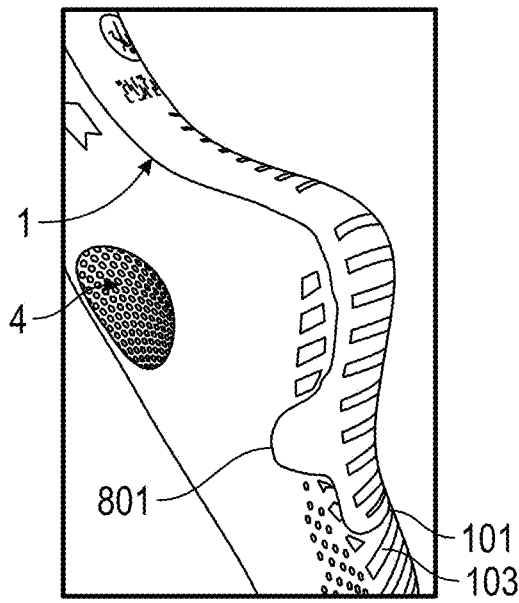
Figure 10:
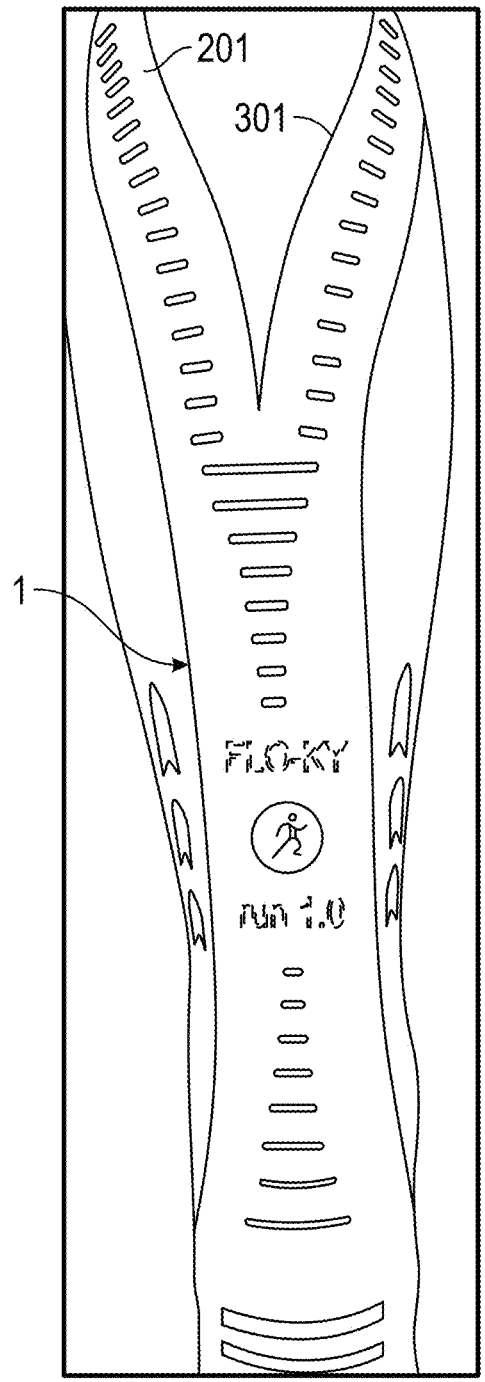
FIGS. 10 to 13 show various details of the leg area of the stocking according to the previous figures, in a worn condition.
Figure 11:
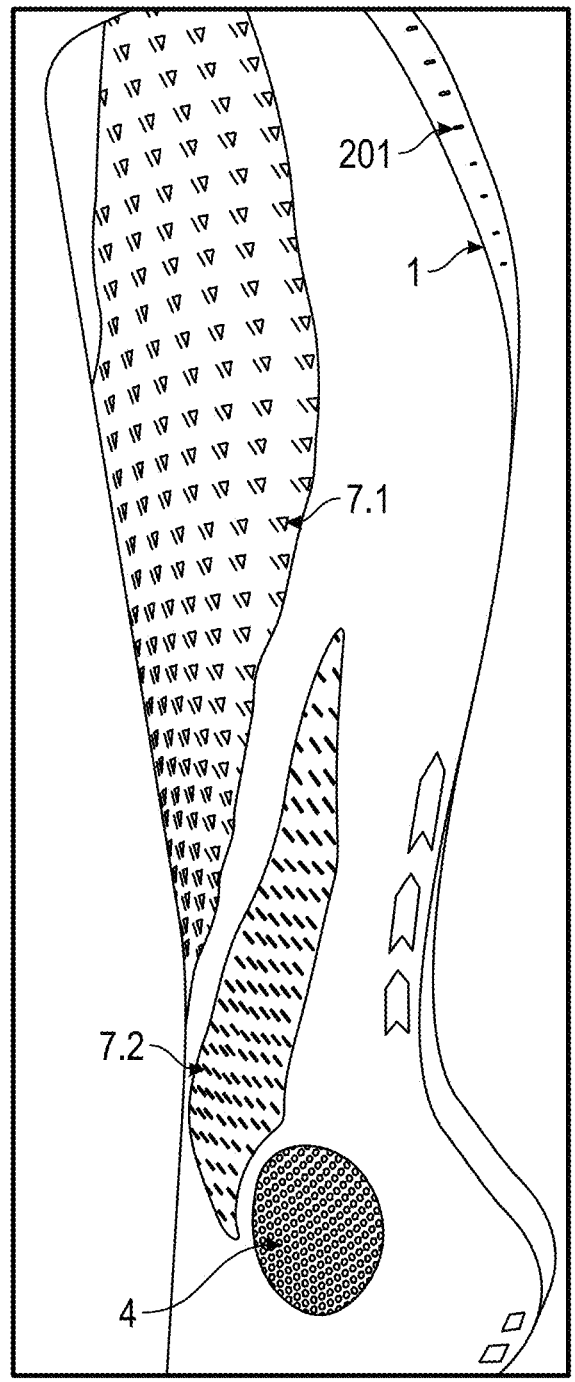
Figure 12:
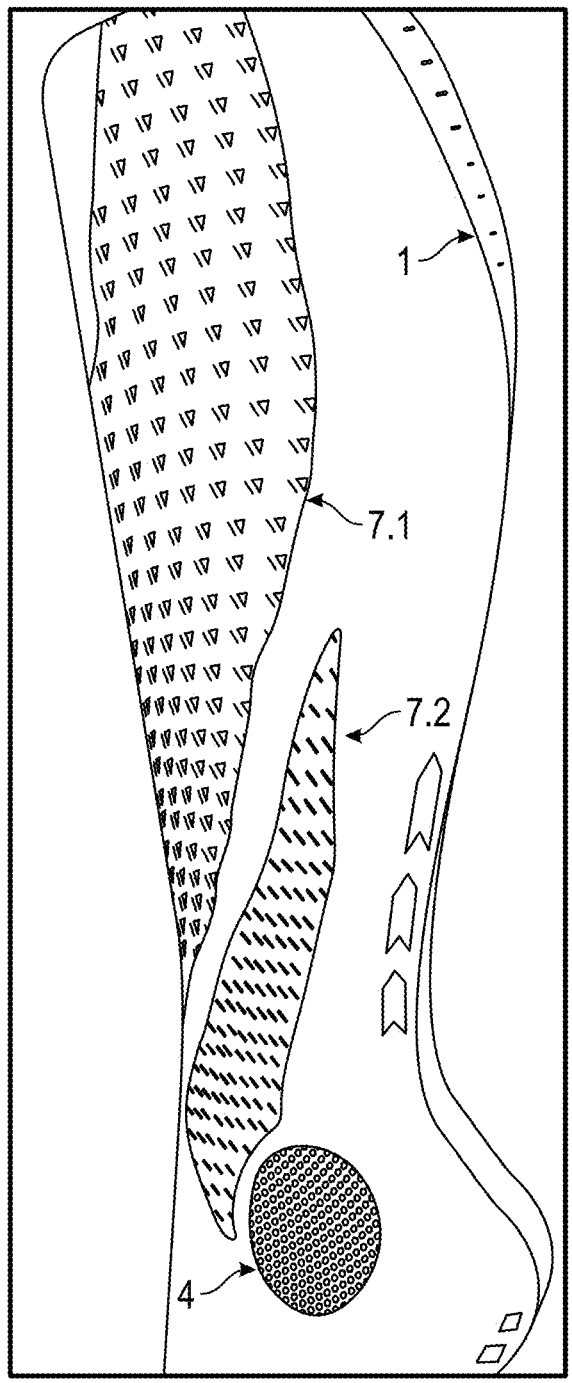
Figure 13:
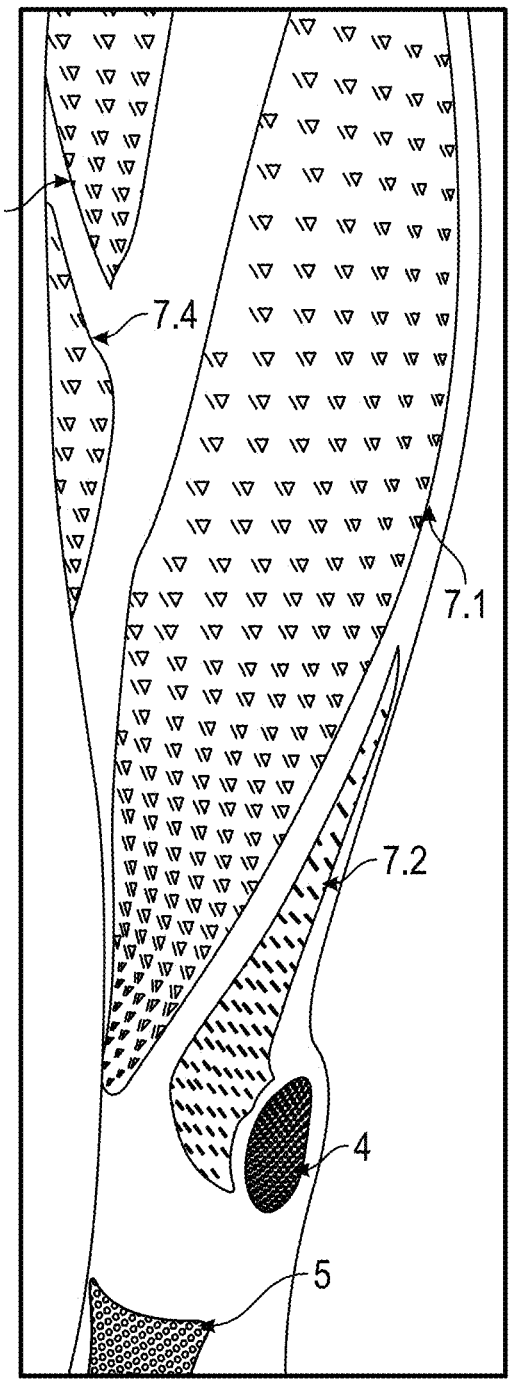
Figure 14:
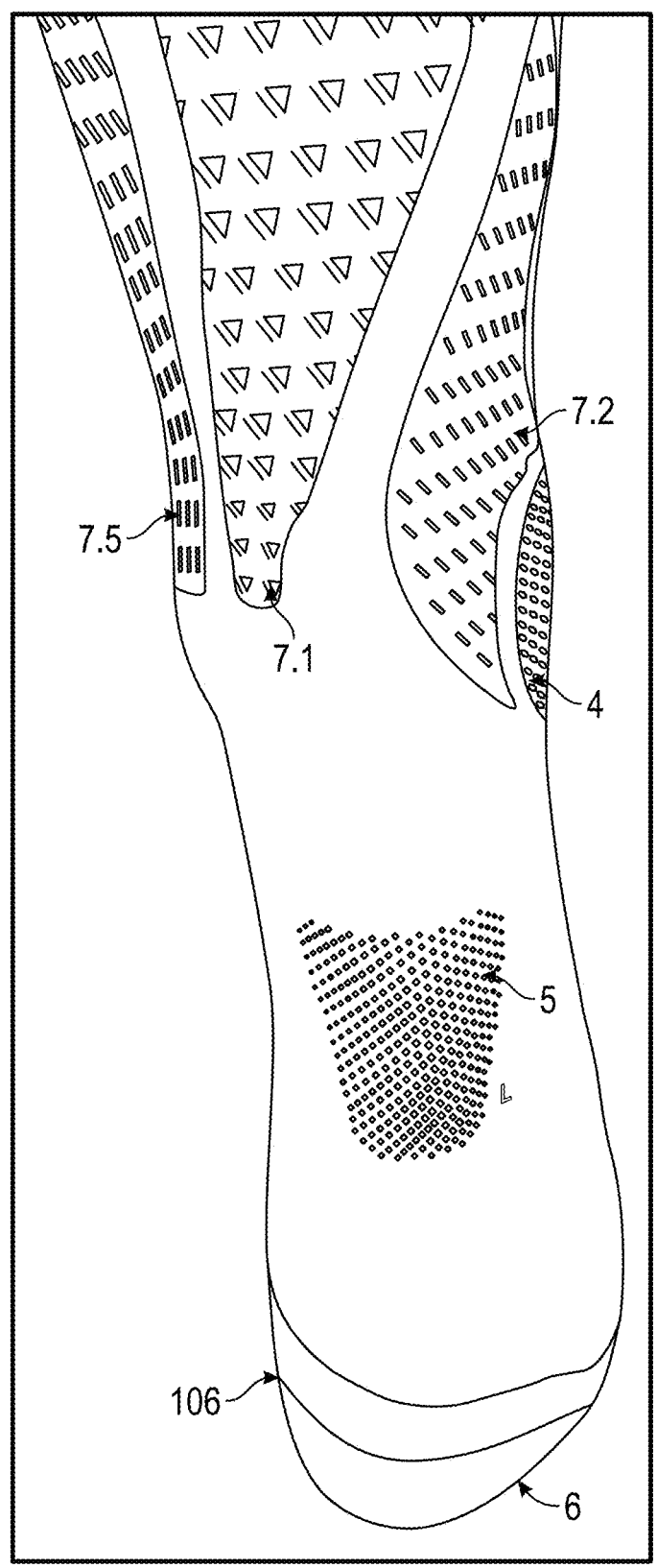
FIG. 14 shows a detail of the sock on the dorsal area of the foot.

FIGS. 2 and 3 show a pair of socks according to the present invention respectively from the side corresponding to the front side of the foot and leg and from that corresponding to the rear/lower side of the foot and leg.

The illustrated sock can be made as already described above using any manufacturing process known or to be developed in the future.

In a non-limiting but preferred way, in the illustrated embodiment the sock is made in the form of a tubular garment, i.e. without a pre-shaping of the heel part in an unworn condition.

Furthermore, again according to the illustrated executive example and in a non-limiting way, the sock is made of a knitted fabric. The yarn used can be of any type consisting of one or more natural fibers, one or more synthetic fibers and a combination of said natural and synthetic fibers.

In a preferred embodiment, the thread used is of plastic material obtained from the recycling of plastic material.

As can be seen from FIGS. 2 and 3, along the part of the fabric of the sock intended to overlap the sole of the foot and the rear side of the leg there is a band of material indicated with 1 which extends in the longitudinal direction of the tubular shape of the fabric that forms the sock. According to a characteristic of the illustrated embodiment, an end 101 of said band 1 is provided in the terminal area of the plantar arch on the side facing the end of articulation to the metatarsals.

The extension along the plantar arch is defined in such a way that the said band substantially extends over the entire Lejars venous sole and/or the entire triangle of the vault (as defined in FIGS. 1.3 and 1.4).

The said band extends seamlessly towards the heel, turning around the same and goes up the leg overlapping the area of insertion of the Achilles tendon and the calf, while the said band bifurcates into two terminal sections diverging from each other in a V-shape, each in the direction of an opposite side of the leg. The said two branches 201, 301 extend so as to follow the conformation of the calf muscles, that is, in particular so that one branch of the bifurcation is in correspondence with the medial twin muscle and the other branch at the level of the lateral twin muscle.

The band of material is applied by chemical/physical adhesion and/or sewing, preferably by molding and in particular by screen printing on the corresponding area of the material of the knitted fabric that forms the sock and advantageously on the external face of said fabric, i.e. the opposite face to that of contact with the foot and leg.

The band is constituted by plastic material having a greater rigidity and shape memory than the knitted fabric of the sock, preferably but not exclusively by silicone and in particular by silicone with shape memory.

By way of example and without limitation, the thickness of said band can vary from about one mm to a few tens of microns and is preferably between 30 and 70 micrometers, in particular of about 50 micrometers.

As is evident in the example illustrated, the width of the band is about a few centimeters while this width is substantially halved at the two terminal bifurcation sections 201, 301.

According to a possible embodiment variant, the thickness and/or width of said band 1 can vary along its extension both in the longitudinal direction and in the transverse direction in order to generate mechanical responses diversified by application areas, i.e. overlapping a part of the foot or leg.

According to a still further possible variant, in addition to silicone, it is possible to use one or more of the plastics materials described above and/or combinations, or mixtures thereof.

Still according to possible executive variants, the overall width of the band or strip is between 1 cm and 8 cm, more preferably between 2 cm and 6 cm to ensure correct support and sustain for the ankle joints and its soft tissues.

As already anticipated in the previous description, the combination of the action of the zones of greater thickness, i.e. of the thickening zones of the sock wall obtained by means of the thickening elements constituted by said band, allow to produce different biomechanical, vascular and neurological effects that have both therapeutic efficacy, and preparatory efficacy to preserve the foot and leg against damage from work stress, and a further efficacy to increase and/or optimize the mechanical and/or physiological functions of the foot and leg allowing to obtain better performance.

While the knitted fabric of the sock has as its first, but not the only function, the function of extending elastically adhering to the foot and the leg so as to hold the aforementioned band that forms the thickening element in the correct position, the greater rigidity, i.e. the elastic coefficient of expansion and the greater elastic resistance to bending or the greater rigidity of this band allow to obtain the following biomechanical functions:

Improved localized compression on the Lejars venous insole resulting in:
1) better muscle oxygenation and faster recovery;
2) less muscle fatigue and pain typical of efforts;
3) increase in muscle power;
4) better resistance;
5) reduction of the risk of injury to muscle fibers;

"Taping" and shimming function:
1) increased squeezing also in the calf area and greater muscle oxygenation;
2) decrease in vibrations with consequent lower possibility of inflammation of the Achilles tendon;
3) decrease in calf fatigue;
4) less chance of falling of the 5th metatarsal, and improvement of posture during running;
5) protection from vibrations due to contact with the ground and therefore protection against microtrauma;
6) increase of the binding on the back of the shoe and therefore increase of the stability during running;
7) unloading of the Achilles tendon with reduction of effort during running.

The provision of the band on the external face of the knitted fabric, or on the face of said fabric opposite to the one adhering to the foot and the leg and the absence of seams, allows to avoid internal contact areas that can generate abrasions and/or blisters.

The use of an application by printing and in particular by screen printing allows the creation of a lighter sock with consequent less sweating of the foot, consequently decreasing the possibility of skin maceration effects.

With reference to perspiration, the illustrated embodiment shows, by way of non-limitative way, the openings passing through the layer of material which form the material band 1. Said openings indicated with 601 are distributed according to a predetermined pattern along the surface extension of the band 1 and guarantee a perspiration effect of sweat.

With reference to yet another feature, the band 1 has in its terminal area intended to overlap the Lejars venous insole two opposite lateral extensions 701, 801. One of these extends from the lateral edge of the band 1 towards the inner side of the foot and the other towards the outside. The first extension 701 towards the inner side of the foot overlaps the area of the plantar arch and more precisely in the median area of the plantar arch with reference to the longitudinal extension of the same and provides a supporting effect of the plantar arch.

The opposite extension and facing the outer side of the foot indicated with 801 overlaps the area of the root of the 5th metatarsal and provides a support effect of the said root of the 5th metatarsal.

According to another characteristic of the present embodiment, a thickening element indicated with 2 is provided in the area of the 5th metatarsal.

This thickening element can be constituted by a layer of material similar to that of the band 1 and can have a thickness similar to that of the band 1, according to one or more of the previous embodiments and variants described. However, the thickness of said element 2 and the type of material, or the corresponding mechanical characteristics, are not required to be identical to those of the material of the band 1.

This thickening element 2 helps to modify the thicknesses under the sole of the foot in a differentiated way and to reproduce or follow or favor the foot propeller movement that the foot performs during running or walking.

Without this constituting a limitation, the preferred executive example shows in combination with the said thickening element 2 associated with the 5th metatarsal an area provided with anti-slip material on the opposite side of the foot, i.e. in correspondence with the first metatarsal.

The said area is indicated with 3 and in the illustrated embodiment extends from the end of the band 1 to the tip of the foot.

According to one feature, said zone provided with anti-slip material extends for substantially the entire width of the band 1 at the end thereof while it moves towards the inner side of the foot, narrowing towards the first metatarsal and then coinciding with the first phalanx towards the end of the foot.

In said anti-slip zone 2, on the outer side of the knitted fabric of the sock, a material which has a higher coefficient of friction with respect to the fabric of the sock, relative to the shoe, is applied, preferably, but not limited to by means of molding, in particular by screen printing. This material with a higher coefficient of friction is applied discontinuously on the fabric of the sock, i.e. in different areas separated from each other which have a specific shape and specific dimensions, as well as a specific relative position according to a predetermined design.

In order to harmonize the effect of greater adhesion or gripping of said areas with the foot helix movement, the material in area 3 is applied with different distribution patterns in three successive areas starting from the end of the band 1 towards the tip of the foot.

The preferred distribution design provides that directly adjacent to the end of the band 1 the anti-slip material is applied in the form of strips 103 substantially parallel and oriented in a transverse direction to the longitudinal axis of the foot. In the area coinciding with the first phalanx, the said strips of non-slip material 203 are instead always oriented parallel to each other in a direction parallel to the longitudinal axis of the foot, while in the end zone, i.e. on the tip of the foot, the said strips of anti-slip material 303 they are again oriented transversely to the longitudinal axis of the foot and substantially parallel to those 103 of the one directly adjacent to the end of the band 1.

The remaining part of the insole may consist only of the material of the fabric that forms the sock or it may also include elements of non-slip material that are distributed in the form of small dots or pois equidistant from each other.

The different thicknesses of the thickening and non-slip zones distributed on the sole of the foot and their different coefficient of friction are such as to further improve the reproduction of the foot propeller movement thus favoring the movement of the foot during running and thus creating an aid in motion and therefore an improvement in performance;

Areas of non-slip material indicated with 4 and 5 are also provided in other parts of the sock as indicated in FIGS. 3, 5, 9, 14.

In the example shown in these areas, the anti-slip material is applied in the form of small areas or dots, so-called polka dots that are distributed evenly over an area coinciding with the outer side of the ankle and with the dorsal insole of the shoe.

As is evident in this case, the density of said areas is greater than in the area of the sole of the foot and said density can be different from area to area.

As regards the anti-slip material, this can be selected from one or more materials such as rubber, silicone, plastics and mixtures of these materials, preferably applicable by printing, in particular by screen printing.

Thanks to the aforementioned areas provided with antislip material, the sock according to the present invention allows to obtain various functions, including in particular:
1) less slipping of the foot in the shoe;
2) increase of proprioception with the road surface;
3) lower risk of retorts;
4) greater awareness of stability;
5) better thrust in running and walking.

Furthermore, the provision of non-slip silk-screened areas on the dorsal part and near the ankle optimizes the grip with the shoe, preventing the sock from rolling and the consequent loss of improving functions.

According to yet another innovative feature present in the illustrated example, but which can possibly also be omitted by renouncing to the corresponding functions, the fabric that forms the sock can have a different structure in different areas of the same. Said areas are preferably associated with predetermined anatomical areas of the leg or foot. These areas are indicated with 7.1, 7.2, 7.3, 7.4, 7.5 in the illustrated embodiment and the structure of the same can be obtained by applying by printing, in particular by screen printing the material according to different designs and distributions and densities in the corresponding area in order to obtain a greater thickness and/or a greater mechanical resistance to traction and therefore a greater elastic force of return in the condition not subjected to traction and/or an effect of protective cushioning or damping of mechanical stresses. This material can be plastic, silicone or other polymers or mixtures thereof.

According to a particular embodiment, the said zones 7.1, 7.2, 7.3, 7.4, 7.5, of greater thickness and/or mechanical resistance and/or elastic coefficient obtained thanks to a different intertwining of the knitted fabric of the sock, are foreseen to coincide with the zones of the tibial and/or peronal musculature. The illustrated embodiment shows that said zones have a spindle-shaped position and shape that corresponds to that of a muscle bundle or a group of muscle bundles of the tibial and/or peronal area.

Furthermore, in the terminal end, the stocking has a toe 6. In the upper part, the toe is closed with an upper seam, indicated by 106.

From the foregoing it is evident that the stocking according to the present invention differs substantially from the generic stockings present in the state of the art and that they apply only some of the principles and measures set forth and present in combination in the present invention, since this application is entirely generic and not aimed at obtaining a biomechanical effect harmonized with the effects on circulatory and neurological functions thanks to a combined and functionally harmonized provision of the said devices.

It should be remembered here that the present invention refers to at least two different types of socks that differ in a different length of the quarter. It is important to note that these two alternatives are not to be considered as limiting the invention, but that the length of the quarter can vary between the said two alternatives and/or even be less or greater than that provided for by the two alternatives and that obviously, the length of the thickening element along the quarter will be determined by the length of the quarter itself, as well as the conformation of the areas indicated with 7.1 to 7.5 in the preceding claim.

In particular, one of the two embodiments provides a quarter of such a length as to substantially overlap the entire calf area and which has a thickening element like the one previously described and provided with the upper terminal bifurcation.

The other embodiment, on the other hand, provides for a leg having a shorter length and is related to a so-called American sock. In this case the leg does not extend to the calf area as well, but ends below the calf. A preferred embodiment provides that said quarter overlaps the root zone of the Achilles tendon. In this case, the thickening element will be of shorter length and will end before the bifurcations present in the thickening element associated with the sock with a longer leg and covering the calf. The zones 7.1 to 7.5 on the front side of the sock will also obviously be modified.

The invention claimed is:
1. A sock comprising:
a foot part; and
a leg part,
the foot part being designed to overlap a foot of a user and the leg part being designed to overlap at least one part or an entire part of a leg up to below a knee,
optionally the foot part being closed by a toe part,
said sock being made of a layer of mesh having, one or more areas of said sock, a structural modification element that is applied on said mesh,
wherein the structural modification element consists of a thickening element of a wall of the sock that extends over an entire foot vault or along an entire foot bottom and/or along an entire triangle of the foot vault,
wherein said thickening element extends, without interruption, up to an area of insertion of an Achilles tendon,
wherein the leg part presents a length such as to overlap a calf part ending below the knee, the thickening element extending, without interruption, up to a calf area, where the thickening element divides into two branches that diverge each other towards a lateral leg area,
wherein the two divergent branches of said thickening element after bifurcation extend respectively upwards and so as to follow a conformation of calf muscles, so that a branch of the bifurcation is located at a medial twin muscle and another branch of the bifurcation at a level of a lateral twin muscle,
wherein said thickening element is constituted by a continuous band of material having a predetermined width and a predetermined thickness, said continuous band of material extending seamlessly from an anterior end of an arch of the foot, at an extremity towards metatarsals, up to an opposite end, to ends of the two divergent branches when said thickening element extends up to and along the calf area,
wherein the thickening element is formed by a band or a strip of material associated with a knitted wall of the sock in an area intended to overlap anatomical areas at the foot vault, the entire foot bottom, and/or an triangle of the foot vault, an area of insertion of an Achilles tendon, a material of the thickening element having a lower extensibility than an extensibility of a remaining wall of the sock, and
wherein said band or strip of material is applied to an outside of a knitted fabric that forms the wall of the sock.

2. The sock according to claim 1, wherein a knitted fabric wall of the sock is made according to one or more of the following alternatives:
an elasticized fabric or a fabric made from a plurality of knitting processes so to obtain a graduated compression effect;
a fabric that has different types of weaves distributed on an extension of a knit and has thickness or stiffness modifications with reference to extensibility and shape memory of the fabric, or an elastic return force when not subjected to tension extension; or
weaves of the mesh that generate a breathable effect.

3. The sock according to claim 2, wherein the thickening element or the knitted fabric wall have a perforated or micro-perforated structure that allows a desired level of transpiration.

4. The sock according to claim 1, wherein the sock is tubular and a pre-formed area of the sock corresponding to a heel is missing.

5. The sock according to claim 1, wherein the thickening element is provided with at a lateral extension adapted to be positioned towards an inner side of the foot and in correspondence with a plantar arch area, the lateral extension being configured as a lateral flap of said thickening element which coincides with an area of a medial cuneiform and/or of a scaphoid and which has an arched profile with extrados outwards with respect to thickening element.

6. The sock according to claim 1, wherein said thickening element is provided with a lateral extension adapted to be positioned towards an external side of the foot, and has an arched profile with extrados outwards with respect to said thickening element.

7. The sock according to claim 1, wherein, to a portion of fabric which forms the wall of the sock adapted to be positioned in an area of a sole of the foot, there are associated additional elements for modifying a structure of said wall, which are distributed according to a predetermined pattern, which have effects differentiated from each other in order to reproduce and support a foot propeller movement during running and walking, and wherein the thickening element comprises, alternatively or in combination, one or more of the following sock elements:
a first additional thickening element of the wall of the sock, which is configured to be corresponding and coinciding with an area of a 5th metatarsal;
a second additional, non-slip thickening element with a higher friction coefficient than a knitted fabric of the sock configured to increase a grip of said area of the sole of the foot with a shoe; or
a third additional, anti-slip thickening element with greater friction than the fabric of the sock in an area of a first metatarsal, between a terminal end of a fourth additional thickening element configured to be coinciding with a plantar arch and phalanges;
the sock elements and corresponding application areas being made with a design such as to favor an anti-slip or greater grip action between the sock and the shoe and a helical movement of the foot during running or walking.

8. The sock according to claim 7, wherein an application area of the third additional, anti-slip thickening element includes a first area coinciding with a foot end, which has at least one band or strip oriented transversely to a longitudinal extension of a phalanx, an intermediate zone which extends into a connection area of phalanges with a first metatarsal and which has one or more strips or bands of non-slip material oriented in a direction parallel to a longitudinal extension of the phalanges, and a terminal zone flanked at the terminal end of the fourth thickening element coinciding with the foot vault, which is constituted by one or more strips or bands of the non-slip material oriented transversely to the longitudinal extension of the phalanges.

9. The sock according to claim 8, wherein the intermediate zone is between a zone provided with the at least one band or strip of the non-slip material and the terminal end of the fourth additional thickening element in an area of the plantar arch and a thickening zone in correspondence with a 5th metatarsal is provided with a distribution of disks of the non-slip material distributed according to a rectangular distribution grid.

10. The sock according to claim 7, wherein non-slip areas are provided, or areas provided with elements with a higher friction coefficient than a material of the fabric forming the sock, alternatively or in combination, in areas of the sock coinciding with an outside of an ankle and/or with a dorsal part of the foot coinciding with a tongue of the shoe.

11. The sock according to claim 1, wherein a fabric forming the sock has a different structure in different areas of the sock that are associated with predetermined anatomical areas of a leg or the foot, the different structure being obtained by applying a print of a material according to different designs and distributions and densities in corresponding area in order to obtain an area of greater thickness and/or greater mechanical resistance to traction, and of a greater elastic force of return in a condition not subjected to traction and/or an effect of shock absorption, said predetermined anatomical areas being provided to coincide with areas of a tibial and/or peronal musculature when the sock is worn.

12. The sock according to claim 11, in which said predetermined anatomical areas have a spindle-shaped position and shape which corresponds to a shape of a muscle bundle or a group of muscle bundles of the tibial and/or peronal area.

* * * * *